United States Patent [19]

Ernst

[11] Patent Number: 4,590,285

[45] Date of Patent: May 20, 1986

[54] PROCESS FOR PREPARING A MIXTURE OF TETRAHYDROFURAN AND 3-ALKYL TETRAHYDROFURAN AND COPOLYMERS THEREOF

[75] Inventor: Richard E. Ernst, Kennett Square, Pa.

[73] Assignee: E. I. Du Pont de Nemours and Company, Wilmington, Del.

[21] Appl. No.: 671,874

[22] Filed: Nov. 15, 1984

Related U.S. Application Data

[62] Division of Ser. No. 502,317, Jun. 8, 1983.

[51] Int. Cl.$^4$ .................... C07C 31/18; C07D 307/08
[52] U.S. Cl. ..................................... 549/509; 549/429
[58] Field of Search ................................ 549/509, 429

[56] References Cited

U.S. PATENT DOCUMENTS

| | | | |
|---|---|---|---|
| 3,358,042 | 12/1967 | Dunlop et al. | 568/612 |
| 3,560,576 | 2/1971 | Kirchner | 568/855 |
| 3,859,369 | 1/1975 | Copelin | 568/863 |
| 4,120,850 | 4/1981 | Pechhold | 549/509 |
| 4,197,248 | 4/1980 | Copelin et al. | 549/509 |

FOREIGN PATENT DOCUMENTS 1242358  8/1971  United Kingdom .

*Primary Examiner*—Morton Foelak
*Assistant Examiner*—M. L. Moore

[57] ABSTRACT

A mixture of 1,4-butanediol and 2-alkyl-1,4-butanediol is produced by catalytic hydrogenation and reaction with an aldehyde. Such mixture is cyclized to a mixture of tetrahydrofuran and 3-alkyl tetrahydrofuran. Copolymers can then be made from such mixtures of furans.

12 Claims, No Drawings

PROCESS FOR PREPARING A MIXTURE OF TETRAHYDROFURAN AND 3-ALKYL TETRAHYDROFURAN AND COPOLYMERS THEREOF

CROSS-REFERENCE TO RELATED APPLICATION

This application is a divisional of application Ser. No. 502,317, filed June 8, 1983.

DESCRIPTION

1. Technical Field

This invention relates to a process for the preparation of 2-alkyl-1,4-butanediols. It is more particularly directed to a process for preparing such butanediols from 1,4-butynediol or 1,4-butenediol by catalytic hydrogenation and reaction with an aldehyde.

2. Background and Summary of the Invention

The 2-alkyl-1,4-butandiols, especially 2-methyl-1,4-butanediol, are a useful class of compounds in that they can be cyclized to the corresponding 3-alkyltetrahydrofurans, which in turn can be copolymerized with tetrahydrofuran to form polyethers useful in preparing polyurethane elastomers.

In the past, these 2-alkylbutanediols have been prepared by the reduction of itaconic acid, or by the hydroformylation and hydrogenation of 1,4-butenediol described by Copelin in his U.S. Pat. No. 3,859,369.

It has now been found, according to the process of this invention, that 2-alkylbutanediols can be prepared from 1,4-butynediol or 1,4-butenediol by catalytic hydrogenation and reaction with an aldehyde. It is believed that the process proceeds according to the equations

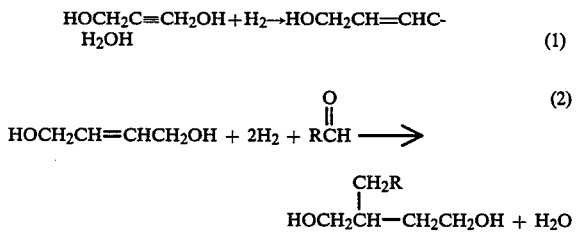

where R is hydrogen or an alkyl radical of 1–4 carbon atoms.

When the starting material is butynediol (equation 1), intermediate butenediol is produced, which is further hydrogenated to the product 2-alkyl-1,4-butanediol. The same product can also be made by using the butenediol as the starting material and omitting the step of equation 1 entirely.

In either case the reaction is conveniently conducted by bringing together, at an initial pH of about 9–14, and at a temperature and pressure suitable for reaction, the butynediol or butenediol, hydrogen, an appropriate aldehyde, and a suitable hydrogenation catalyst.

When butynediol is used as the starting material, the process may be run by itself, but it has been found, surprisingly, that it can also be run simultaneously with and in the same reaction vessel as the process shown in British Pat. No. 1,242,358, according to which 1,4-butanediol is produced from 1,4-butynediol by catalytic hydrogenation using Raney nickel as the catalyst.

Whether the process is run by itself or not, or whether it begins with butynediol or butenediol, the process produces a mixture of 1,4-butanediol and a 2-alkyl-1,4-butanediol. While these can be easily separated by conventional procedures, it may be desirable to keep the mixture intact for it can be cyclized in one step to give a mixture of tetrahydrofuran and a 3-alkyltetrahydrofuran. A tetrahydrofuran/3-alkyltetrahydrofuran copolymer can then be prepared directly from this mixture by adding a suitable catalyst and holding the mixture under conditions suitable for copolymerization.

DETAILED DESCRIPTION OF THE INVENTION

The process of the invention can be run batchwise, but is more conveniently and preferably run continuously.

In the continuous mode, a column reactor of appropriate dimensions is packed in the usual manner with a conventional hydrogenation catalyst. Suitable catalysts are, for example, platinum, Raney nickel and cobalt. Raney nickel, especially Raney nickel from which about 25% by weight of aluminum has been removed, is preferred. The catalyst may be in any convenient form, but is ordinarily and preferably granular.

The butynediol used may be any commercially available type, and may be, for example, that obtained by catalytically reacting acetylene and formaldehyde, using a copper acetylide complex as the catalyst, as described in U.S. Pat. No. 3,560,576 to Kirchner.

The butenediol, if that is used as a starting material, can likewise be of any commercially available type, and may be, for example, that obtained by the conventional hydrogenation of butynediol.

The pH value of the butynediol or butenediol is adjusted to the range 9–14, preferably about 10–11, and is then fed continuously through the reaction column.

The aldehyde, ordinarily as an aqueous solution, is also fed continuously through the column. The aldehyde will be one having the structure shown in equation (1), and will preferably be formaldehyde.

Enough aldehyde is fed into the column to provide a diol/aldehyde weight ratio of 2/1 to 200/1, preferably 10/1 to 25/1.

If the butynediol is obtained by the previously mentioned Kirchner method, it may already contain the proper amount of formaldehyde as an impurity, and separate addition of formaldehyde to the column may be unnecessary.

Hydrogen is continuously fed into the column, in co-current or countercurrent flow to the other reactants, and is maintained in the column at a pressure of 6895–55160 kPa (gauge), preferably 34475 kPa (gauge).

The exit temperature of the reaction mass is maintained at 100°–200° C., preferably about 140°–150°, by recycling according to well known chemical engineering principles.

Flow of reactants into the reactor is regulated to give them a residence time in the reactor of 30–200 minutes, preferably 100–120 minutes.

The 2-alkylbutanediol is removed from the column in liquid form, as a mixture with 1,4-butanediol. The alkylbutanediol can be separated from the 1,4-butanediol, if one wishes to do this, by fractional distillation conducted according to well known chemical engineering principles.

The process of the invention, when run in the batch mode, is conducted under basically the same conditions, using the proportions of reactants and the recovery procedures just described.

Whether run batchwise or continuously, the 2-alkyl-butanediol produced may be catalytically cyclized to a corresponding 3-alkyltetrahydrofuran, using sulfuric acid as the catalyst, by the general method disclosed in U.S. Pat. No. 3,726,905 to Coates and Reilly. If the product, a mixture of 1,4-butanediol and 2-alkyl-1,4-butanediol, is kept intact as it comes from the reaction column, both components can be simultaneously cyclized using this method, to give a corresponding mixture of tetrahydrofuran and 3-alkyltetrahydrofuran.

This mixture, or one like it made by mixing separate components, can then be copolymerized to form a tetrahydrofuran/3-alkyltetrahydrofuran copolymer using fluosulfonic acid as the catalyst, as disclosed in U.S. Pat. No. 3,358,042 to Dunlop and Sherman. This copolymer can then be used to prepare a polyurethane by the general method disclosed in U.S. Pat. No. 4,120,850 to Pechhold.

EXAMPLES

In the following examples, all parts are by weight.

EXAMPLE 1

Into a fixed-bed column reactor 76 cm long, with an inside diameter of 4.5 cm, were packed 1000 gm of Raney nickel alloy 25% of whose aluminum had been removed with caustic.

1,4-Butynediol, a 50% aqueous solution containing 0.4% of formaldehyde, prepared as shown in U.S. Pat. No. 3,560,576, was brought to pH 11 with sodium hydroxide and then continuously fed into the bottom of the column at a rate of 9 ml per minute.

Hydrogen was pumped into the bottom of the column and maintained in the column at a pressure of about 34475 kPa (gauge).

The exit temperature of the product was maintained at about 140° C. by recycling.

The product, a 1/20 mixture of 2-methyl-1,4-butanediol and 1,4-butanediol, and also containing a small amount of butanol, was removed from the top of the column at a rate of 9 ml per minute.

EXAMPLE 2

Into a shaker tube were charged

| | |
|---|---|
| 1,4-butynediol (50% solution in water) | 40 parts |
| Formaldehyde (37% solution in water) | 4 parts |
| Sodium hydroxide (50% solution in water) | 0.6 part |
| Raney nickel (slurry grade, from which substantially all aluminum had been removed) | 5 parts |

The resulting slurry had a pH of 11–12.

The slurry was heated to and held at 150° C. and a hydrogen pressure of 34475 kPa (gauge), and shaken for one hour.

The product was a mixture the organic portion of which was composed of 13.2% 2-methyl-1,4-butanediol, 76.7% 1,4-butanediol, and minor amounts of methanol and butanol.

EXAMPLE 3

Twenty ml of product like that produced in Example 1, and composed of 2.3% of 2-methyl-1,4-butanediol, 42% of 1,4-butanediol and the remainder water and a small amount of impurities, was distilled until the pot temperature reached 150° C. The residue was cooled to 100° C., and to it was then added 0.25 ml of concentrated sulfuric acid.

This mixture as heated to 115° C. and held there for about 30 minutes, while the product, the organic portion of which contained 8.4% of 3-methyltetrahydrofuran and 91.6% of tetrahydrofuran, distilled off.

EXAMPLE 4

Into a shaker tube were charged

| | |
|---|---|
| 1,4-Butenediol (50% solution in water) | 40 parts |
| Formaldehyde (37% solution in water) | 2 parts |
| Sodium hydroxide (50% solution in water) | 0.6 part |
| Raney nickel (slurry grade, from which substantially all aluminum had been removed) | 5 parts |

The resulting slurry had a pH of 11.9.

The slurry was heated to and held at 140° C. and a hydrogen pressure of 20,684 kPa (gauge) and shaken for 2 hours.

The product was a mixture the organic portion of which was composed of 10.4% 2-methyl-1,4-butanediol, 73.5% 1,4-butanediol and minor amounts of methanol and butanol.

I claim:

1. In the method of preparing tetrahydrofurans by cyclizing diols, the improvement comprising using a mixture of 1,4-butanediol and 2-alkyl-1,4-butanediol produced by bringing together, at an initial pH of 9–14, and a temperature and pressure suitable reaction,
   (a) hydrogen,
   (b) hydrogenation catalyst, and
   (c) 1,4-butynediol or 1,4-butenediol, and an aldehyde of the structure

R—CHO where R is hydrogen or an alkyl radical of 1–4 carbon atoms,
   in a butynediol or butenediol/aldehyde weight ratio of 2/1 to 200/1.
2. A method for preparing a copolymer of tetrahydrofuran and 3-alkyltetrahydrofuran, the method comprising adding a suitable polymerization catalyst to the mixture produced by the method of claim 1 and holding the mixture under conditions suitable for polymerization.
3. The method of claim 1 wherein the butynediol or butenediol/aldehyde weight ratio is 2/1 to 27/1.
4. The method of claim 1 wherein the butynediol or butenediol/aldehyde weight ratio is 2/1 to 25/1.
5. The method of claim 1 wherein the butynediol or butenediol/aldyhyde weight ratio is 10/1 to 25/1.
6. The method of claim 3 wherein the aldehyde is formaldehyde.
7. The method of claim 6 wherein the pH is 10–11.
8. The method of claim 2 wherein the butynediol or butenediol/aldehyde weight ratio is 2/1 to 27 to 1.
9. The method of claim 2 wherein the butynediol or butenediol/aldehyde weight ratio is 2/1 to 25/1.
10. The method of claim 2 wherein the butynediol of butenediol/aldehyde weight ratio is 10/1 to 25/1.
11. The method of claim 8 wherein the aldehyde is formaldehyde.
12. The method of claim 11 wherein the pH is 10–11.

* * * * *